(12) United States Patent
Zhao et al.

(10) Patent No.: US 10,575,537 B2
(45) Date of Patent: Mar. 3, 2020

(54) SAURY MAILLARD PEPTIDE AND ITS PREPARATION METHOD AND APPLICATION

(71) Applicant: South China University of Technology, Guangzhou (CN)

(72) Inventors: Mouming Zhao, Guangzhou (CN); Qiangzhong Zhao, Guangzhou (CN); Guowan Su, Guangzhou (CN); Yang Liu, Guangzhou (CN); Lianzhu Lin, Guangzhou (CN); Rongzhong Zhao, Guangzhou (CN)

(73) Assignee: South China University of Technology, Guangzhou, Guangdong (CN)

( * ) Notice: Subject to any disclaimer, the term of this patent is extended or adjusted under 35 U.S.C. 154(b) by 189 days.

(21) Appl. No.: 15/554,396

(22) PCT Filed: Dec. 23, 2015

(86) PCT No.: PCT/CN2015/098528
§ 371 (c)(1),
(2) Date: Aug. 29, 2017

(87) PCT Pub. No.: WO2016/138783
PCT Pub. Date: Sep. 9, 2016

(65) Prior Publication Data
US 2018/0042264 A1 Feb. 15, 2018

(30) Foreign Application Priority Data
Mar. 3, 2015 (CN) .......................... 2015 1 0094674

(51) Int. Cl.
| | |
|---|---|
| A23J 1/04 | (2006.01) |
| C07K 14/46 | (2006.01) |
| A23J 3/34 | (2006.01) |
| A23J 3/04 | (2006.01) |
| A61K 38/04 | (2006.01) |
| C07K 1/34 | (2006.01) |
| C12P 21/06 | (2006.01) |
| A23L 33/00 | (2016.01) |

(52) U.S. Cl.
CPC . *A23J 1/04* (2013.01); *A23J 3/04* (2013.01); *A23J 3/34* (2013.01); *A61K 38/04* (2013.01); *C07K 1/34* (2013.01); *C07K 14/461* (2013.01); *C12P 21/06* (2013.01); *A23L 33/00* (2016.08)

(58) Field of Classification Search
None
See application file for complete search history.

(56) References Cited

U.S. PATENT DOCUMENTS 8,653,032 B2 * 2/2014 Rhyu .................. A61K 38/168
514/1.1

FOREIGN PATENT DOCUMENTS

| CN | 1395862 A | | 2/2003 |
|---|---|---|---|
| CN | 101589793 A | * | 12/2009 |
| CN | 101986872 A | | 3/2011 |
| CN | 104337836 | * | 2/2015 |
| CN | 104337836 A | | 2/2015 |
| CN | 104664039 A | | 6/2015 |
| KR | 2009 010634 A | * | 1/2009 |
| KR | 2012 093645 A | * | 8/2012 |

OTHER PUBLICATIONS

Preparation and Application of Low Bitter Soybean Antioxidant Pepide; A Dissertation Submitted for the Degree of Master; Candidate: Li Yinjuan; Supervisor: Prof. Zhao Mouming; South China University of Technology; Nov. 28, 2013.
Effects of Amino Acid Content on Antioxidant Activity of Honey from Different Sources and Geographic Origins; Dong Rui, Zheng Yi-nan; vol. 32, No. 21; 2011.
Preparation and Free Amino Acids Analysis of Enzymatic Hydrolysates from Cololabis Saira; Chen Jian-wen; vol. 28, No. 09; 2007.
Transactions of Oceanology and Limnology; Effects of Temperature on the Chemical Characteristics and Antioxidant Activity of Maillard Reaction Products from the Silver Carp (Hypophthalmichthys Molitrix) Peptides and Glucose; Meng Yanli; 2013.

* cited by examiner

*Primary Examiner* — Ralph J Gitomer
(74) *Attorney, Agent, or Firm* — The Dobrusin Law Firm, PC

(57) ABSTRACT

The present invention discloses a saury Maillard peptide with antihyperuricemic activity and its preparation method and application, with the method comprising the following steps: mincing a saury, adding water, heating, agitating, adjusting a pH value to 4.2, separating by centrifugation, and collecting the precipitate; adding water, proteases and amino acids to the precipitate, adjusting a pH value to 7.0, hydrolyzing, adding a reducing sugar to cause a reaction, centrifuging and collecting a supernatant which is saury Maillard peptide; and spray drying the peptide liquid to obtain a dry powder. The method of the present invention realizes the continuous action of enzymolysis and Maillard reaction to prepare the Maillard peptide, not only simplifying the production process, shortening the production cycle, and reducing the production costs, but also significantly enhancing the antihyperuricemic activity of the produced Maillard peptide. Animal experiments in rats showed that the obtained Maillard peptide prepared by the method of the present invention could significantly decrease the level of serum uric acid in rats, and display certain protective effect in their kidney.

2 Claims, 1 Drawing Sheet

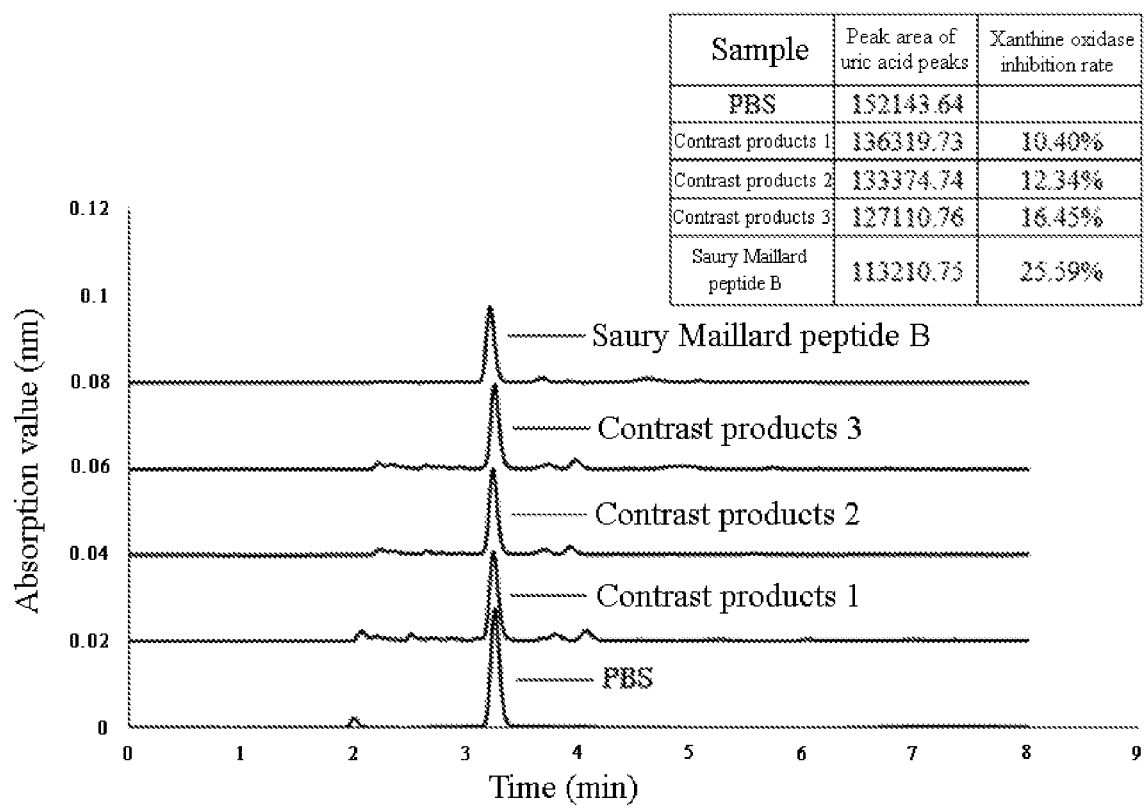

SAURY MAILLARD PEPTIDE AND ITS PREPARATION METHOD AND APPLICATION

FIELD OF THE INVENTION

The present invention relates to a saury Maillard peptide having—antihyperuricemic activity and its preparation method and application.

BACKGROUND OF THE INVENTION

Uric acid is the product of human purine metabolism. Generally, the human serum uric acid level is 200-410 μmol/L, with female usually lower than male. Elevated levels of human uric acid are usually associated with abnormal purine metabolism or abnormal renal excretion, and internationally the concentration of male serum uric acid above 420 μmol/L or female's above 357 μmol/L is defined as hyperuricemia. And hyperuricemia often causes gout. Gout was defined by the Egyptians in the year 2640 BC and was recorded in Hippocrates' medical work in 400 BC. Today, due to changes in diet and lifestyle, the number of hyperuricemia and gout patients increases, and hyperuricemia and gout have become a common rheumatic disease in the modern society.

People are rarely concerned about their own serum uric acid levels and often take no treatments until the gout symptoms appear. At present, the main treatments include anti-inflammatory and analgesic which are operated by medicines such as colchicine and non-steroidal anti-inflammatory medicines, and continuous medication for 1 to 2 weeks can significantly suppress the gout symptoms. Indomethacin can also treat acute gout, and injection of the adrenocorticotropic hormone has a better, more rapid curative effect. Allopurinol, having a clear target of action, is the only commercially available drug for reducing the uric acid production and the serum uric acid level by inhibiting the xanthine oxidase activity, but it has a slow effect and may aggravate the gout symptoms in the initial use. However, the anti-inflammatory, analgesic medicines and the allopurinol with a clear action mechanism have some toxicity and side effects during treatment, and therefore patients who have been suffering from chalkstone are mostly subjected to surgery for removing the chalkstone and correcting the joints. In the treatment of asymptomatic hyperuricemia, doctors recommend adjusting the diet or orally taking some food-borne medicines, so as to achieve the purpose of slowly decreasing the level of serum uric acid.

Protein is an essential nutrient in our daily life and contains a lot of bioactive substances—bioactive peptides, which may have antihypertensive, cholesterol-decreasing, antithrombotic, anticancer, and anti-oxidation activities and other biological activities. However, these bioactive sequences are present within these protein substrates, and when the protein enters the human stomach and intestinal tract while being eaten, these bioactive peptides cannot be released completely by enzymes in the stomach and intestinal tract. The modern biological enzymolysis technology, as a method for efficiently releasing the bioactive peptides inside the protein, is mainly to imitate the proteolytic process of the human body's digestive system. It could efficiently obtain the bioactive peptide with y specific biological activity by modification of hydrolysis conditions as well as type and concentration of the protease, since the hydrolyzation is in vitro reaction.

Besides, Maillard reaction, as a non-enzymatic browning reaction often occurring between reducing sugar and amino acids, peptides, proteins or any nitrogen-containing compounds in the process of food processing or storage, has a fast reaction process and complex internal composition changes and may even produce some substances with strong biological activity, it is widely reported that the Maillard reaction can significantly enhance the anti-oxidation activity of protein peptides, therefore it is also an effective methods of enhancing the biological activity of protein peptides.

Saury, as the middle- and upper-level ocean fish, has rich protein but a lower added value, and is mainly used as inexpensive food or feed. At present, several studies have been reported on the preparation of antioxidant peptides by biological enzymolysis, but there are still lack of studies of using saury to prepare antihyperuricemic components. If saury is used as raw materials to produce protein peptide products that significantly reduce uric acid levels of human, not only the application of saury is expanded and its economic value is improved, but more importantly people's quality of life can be improved, thus having great social significance.

CONTENTS OF THE INVENTION

It is a primary object of the present invention to provide a method of preparing a saury Maillard peptide having antihyperuricemi, which method is innovative in the realization of the continuous action of enzymolysis and Maillard reaction, and the addition of monomer amino acids as the substrate inhibitor of the enzymolytic system to regulated the enzymolytic process.

It is another object of the present invention to provide a saury Maillard peptide having antihyperuricemic activity prepared by the above method.

It is a further object of the present invention to provide the use of the above saury Maillard peptide.

The objects of the present invention are achieved through the following technical solution:

A method of preparing a saury Maillard peptide having antihyperuricemic activity is provided, comprising the following steps:

(1) Pretreatment of saury: removing the head and internal organs of the saury, cleaning, mincing over a meat grinder, adding water 3 to 5 times the mass of the minced saury meat, heating and stirring at 40° C. to 50° C. for 1 to 2 h, adjusting the pH value of the system to 4.2, continuing to stir and heat for 1 to 1.5 h, separating by centrifugation, discarding the supernatant and the upper fat, and collecting a precipitate;

(2) enzymolysis-Maillard continuous reaction: adding water 1 to 1.5 times the mass of the saury precipitate to the saury precipitate, then adding protease and monomer amino acids, adjusting the pH value of the system to 7.0, insulatinghydrolyzing at 50° C. to 55° C. for 6 to 9 h, adding reducing sugar, heating at 100° C. to 121° C. for 1.0 to 2.0 h, centrifuging, and taking the supernatant, thus obtaining the saury Maillard peptide solution; vacuum-concentrating the Maillard peptide solution, and spray drying it to obtain a saury Maillard peptide dry powder;

calculated based on the mass of the saury precipitate, the amount of the added protease accounted for 1.5% to 3.0%, the amount of the added monomer amino acids accounted for 0.1% to 0.3%, and the amount of the added reducing sugar accounted for 0.5% to 2.5%;

the pH value of the system was adjusted with 0.5 mol/L NaOH solution or HCl solution;

the centrifugation was carried out at 5000 r/min for 15 to 20 min;

the protease described in step (2) was a commercial alkaline protease and a flavor protease, preferably a Novozymes' alkaline protease (Alcalase 2.4 L) and a Novozymes' flavor protease (Flavourzyme 500 MG);

the monomer amino acids described in step (2) were tyrosine, phenylalanine or tryptophan, preferably tryptophan; and the reducing sugar described in step (2) was glucose, xylose or ribose.

The saury Maillard peptide prepared by the above method can be used for the preparation of antihyperuricemic medicines or health care products; when used, the saury Maillard peptide can be compounded with the Chinese herbal medicines having an antihyperuricemic effect.

The present invention has the following advantages and effects with respect to the prior art:

(1) The present invention, combining the biological enzymolysis and the Maillard reaction technology to prepare the Maillard peptide have an antihyperuricemic effect. First the monomer amino acids is added in the early stage of enzymolysis, which can directly increase the content of certain amino acids in the final hydrolysates and can reversely regulate the enzymolytic process by substrate inhibition of the enzymolytic system to promotes or inhibits the formation of certain amino acids, so as to alter the amino acid composition of the hydrolysate and increase the antihyperuricemic activity or Maillard reactivity of the hydrolysate. Then the reducing sugar is directly added at the end of enzymolysis to directly initiate subsequent reaction of the Maillard reaction for the preparation of Maillard peptide, which not only simplifies the production process, shortens the production cycle and reduces the production costs, but also significantly enhances the antihyperuricemic effect of the target Maillard peptide. Animal experiments in rats showed that the Maillard peptide prepared by this method could significantly decrease the serum uric acid level of rat and display some kidney protective effect.

(2) The present invention has several advantages, such as simple process operation, low production costs, no pollution and strong antihyperuricemic activity of the resulting Maillard peptide.

BRIEF DESCRIPTION OF THE DRAWINGS

FIG. 1 displays the chromatogram of uric acid peaks for Example 2 and contrast products.

DETAILED DESCRIPTION OF THE EMBODIMENTS

The present invention will be further described in detail below with reference examples and FIGURES; however, the embodiments of the present invention are not limited thereto.

In the following examples, a method of determining the uric acid value by the reversed-phase high-performance liquid chromatography is as follows:

(1) Preparation of solutions 0.2 mol/L (pH 7.5) phosphoric acid buffer (PBS): Accurately weighing 30.0838 g of $Na_2HPO_4 \cdot 12H_2O$ and 2.4962 g of $NaH_2PO_4 \cdot 2H_2O$, and dissolving them with deionized water to a constant volume of 500 ml.

Xanthine solution: Accurately weighing 6.4 mg of xanthine, first dissolving it with 1 ml of 1 M NaOH, then adding 100 ml of PBS, and adjusting the pH value to 7.5 with 1M HCl.

Xanthine oxidase: Taking 120 µl of an enzyme solution, and diluting it to 8 ml with PBS.

Uric acid standard curve: Accurately weighing 10 mg of uric acid, adding 10 ml of water, and then diluting it to 0.1-0.9 mg/ml.

Ammonium acetate-glacial acetic acid: Accurately weighing 3.85 g of ammonium acetate to a constant volume of 1000 ml, and then adding 4 ml of glacial acetic acid.

(2) Sample pretreatment:

Diluting the sample to 40 mg/ml, adding successively 50 µl of the sample and 50 µl of xanthine in a 96-well microplate, with 3 parallels for each sample, adding 150 µl of xanthine oxidase after insulation at 37° C. for 10 min, adding 80 µl of 1M HCl to stop the reaction after continuing insulation at 37° C. for 20 min, filtering through a 0.25 µm aqueous filter till use.

Chromatographic column: Zorbax Eclipse XDB-C18 column (5 µm, 4.6×250 mm, Agilent); and Mobile phase conditions: the eluent was 10% methanol+ 90% ammonium acetate-glacial acetic acid solution, the admission volume was 20 µl, the flow rate was 1 ml/min, the detection wavelength was 290 nm, and the run duration was 10 min.

(3) Calculation formula $$\text{Xanthine oxidase inhibition rate} = (A_0 - A)/A_0 \times 100\%$$

where:

$A_0$—the peak area of the uric acid peak of a sample without addition of peptides analyzed by high-performance liquid chromatography, A—the peak area of the uric acid peak of a sample with addition of peptides analyzed by high-performance liquid chromatography.

As the index in the following examples, the experimental method of therapeutic effects of the peptide samples on the oteracil potassium-induced hyperuricemia in rats was as follow:

(1) Experimental materials

Animals: 140 SPF grade SD male rats, weight 200±20 g, purchased from Laboratory Animal Center of Guangzhou University of Chinese Medicine.

Medicines and reagents: Allophylline tablets (Guangdong Bidi Pharmaceutical Co., Ltd.); oteracil potassium (Shandong Zhongke Taidou Chemical Co., Ltd.); sodium carboxymethyl cellulose (Shanghai Celluloid Plant); and a uric acid kit (Nanjing Jiancheng Bioengineering Research Institute).

Instruments: TGL-16G high-speed refrigerated centrifuge (Shanghai Anting Scientific Instrument Factory); and a multifunctional microplate reader for ELISA (BioTelc USA, Synergy HT).

Animal feeding situations: Animals were bred in SPF grade Laboratory Animal Center of Jinan University, with rat feed and excipients all provided by the same. Housed under conditions of (20±2) ° C. and relative humidity of (60-70) % with a 12 h light-dark cycle and standard diet and water. (2) Experimental method Animal grouping and modeling: Taking a total of 140 healthy male SD rats, and randomly dividing them into a normal control group (20 rats) and a model group (120 rats); the model group rats were gavage with oteracil potassium (daily dose: 2 g/kg) for 7 days, then the rat were anesthetized via intraperitoneally injecting 3% pentobarbital sodium (30 mg/kg) after the last administration, their blood was taken from conjunctival (0.5 ml), then centrifuging at 4° C. and 3000 r/min for 15 min, and taking the upper serum to determine the uric acid content, and the rats in the normal control group were treated with a constant volume of solvent by intragastric administration. The rats with the uric acid content above 110 μmol/L were identified to be successful in modeling.

The rats successful in modeling, according to the uric acid content, was randomly dividing into a model control group (constant volume solvent), a tested peptide sample group (200 mg/kg) and an allopurinol group (50 mg/kg) at 14 rats per group, and the rats were gavage with oteracil potassium (daily dose: 2 g/kg) at a dose of 10 ml/kg, with the model rats treated with a constant volume of distilled water. Administering 3% pentobarbital sodium (30 mg/kg) for 50 min at the end of administering the above-mentioned peptide samples for 10 days and 20 days, drawing the conjunctival blood (0.5 ml), and determining the serum uric acid content; after the 30th day of treatment with anti-gout peptides, drawing the celiac artery blood 5 ml after anesthesia with 3% pentobarbital sodium, and determining the content of serum creatinine and urea nitrogen in addition to determining the serum uric acid content.

Determination of serum uric acid: using the tungstic acid method and strictly following the determination method from the kit instructions.

Determination of serum urea nitrogen and creatinine: Determining the serum urea nitrogen content by the diacetyl oxime method; and determining serum creatinine content by the picric acid method, with the specific operation strictly in accordance with the kit instructions.

Determination of activity of serum xanthine oxidase (XOD) and adenosine deaminase (ADA): Taking 100 μl of serum for determination of XOD, and taking 20 μl of serum for determination of ADA, both in accordance with the kit instructions and operational requirements.

Statistical treatment: all data is presented as "mean±standard deviation", t test was performed to determine the significant difference between samples at the 95% confidence interval using SPSS 19.0 software.

EXAMPLE 1

A method of preparing a saury Maillard peptide having antihyperuricemic activity is provided, comprising the following steps:

(1) Pretreatment of saury: removing the head and internal organs of the saury, cleaning, mincing over a meat grinder, adding water 3 times the mass of the minced saury meat, heating and stirring at 40° C. for 2 h, then adjusting the pH value of the system to 4.2 with HCl (0.5 mol/L), continuing to stir and heat for 1 h, separating by centrifugation (5000 r/min, 15-20 min), discarding the supernatant and the upper fat, and collecting the precipitate;

(2) enzymolysis-Maillard continuous reaction: adding water 1 time the mass of the saury precipitate to the saury precipitate, adjusting the pH value of the system to 7.0 with 0.5 mol/L NaOH solution, raising the temperature of the saury to 55° C., adding Alcalase 2.4 L of Novazymes, Flavourzyme 500 MG of Novozymes, and tyrosine as much as 0.5%, 1.0% and 0.10% of the mass of the saury precipitate, respectively, insulatingly hydrolyzing at 55° C. for 6 h, adding xylose accounting for 0.5% of the mass of the saury precipitate, heating at 110° C. for 1.5 h, then taking the supernatant after centrifuging at 5000 r/min for 15-20 min, thus obtaining the saury Maillard peptide solution.

(3) vacuum-concentrating the saury Maillard peptide solution to the 30% solid or more, and spray drying, thus obtaining the saury Maillard peptide product A.

The therapeutical effects of the saury Maillard peptide product A on the hyperuricemia in rats induced by oteracil potassium were shown in Tables 1, 2 and 3.

EXAMPLE 2

A method of preparing a saury Maillard peptide having antihyperuricemic activity is provided, comprising the following steps:

(1) Pretreatment of saury: removing the head and internal organs of the saury, cleaning, mincing over a meat grinder, adding water 5 times the mass of the minced saury meat, heating and stirring at 50° C. for 1 h, then adjusting the pH value of the system to 4.2 with HCl (0.5 mol/L), continuing to stir and heat for 1.5 h, separating by centrifugation (5000 r/min, 15-20 min), discarding the supernatant and the upper fat, and collecting the precipitate;

(2) enzymolysis-Maillard continuous reaction: adding water 1.5 times the mass of the saury precipitate to the saury precipitate, adjusting the pH value of the system to 7.0 with 0.5 mol/L NaOH solution, raising the temperature of the saury to 50° C., adding Alcalase 2.4 L of Novazymes, Flavourzyme 500 MG of Novozymes, and tryptophane as much as 0.8%, 1.2% and 0.20% of the mass of the saury precipitate, respectively, insulatingly hydrolyzing at 50° C. for 9 h, adding glucose accounting for 1.5% of the mass of the saury precipitate, heating at 121° C. for 1.0 h, then taking the supernatant after centrifuging at 5000 r/min for 15-20 min, thus obtaining the saury Maillard peptide solution.

(3) vacuum-concentrating the saury Maillard peptide solution to the 30% solid or more, and spray drying, thus obtaining the saury Maillard peptide product B.

The therapeutical effects of the saury Maillard peptide product B on the hyperuricemia in rats induced by oteracil potassium were shown in Tables 1, 2 and 3.

The uric acid peak chromatogram of the saury Maillard peptide product B was shown in FIG. 1.

EXAMPLE 3

A method of preparing a saury Maillard peptide having antihyperuricemic activity is provided, comprising the following steps:

(1) Pretreatment of saury: removing the head and internal organs of the saury, cleaning, mincing over a meat grinder, adding water 4 times the mass of the minced saury meat, heating and stirring at 45° C. for 1.5 h, then adjusting the pH value of the system to 4.2 with HCl (0.5 mol/L), continuing to stir and heat for 1.2 h, separating by centrifugation (5000 r/min, 15-20 min), discarding the supernatant and the upper fat, and collecting the precipitate;

(2) enzymolysis-Maillard continuous reaction: adding water 1.2 times the mass of the saury precipitate to the saury precipitate, adjusting the pH value of the system to 7.0 with 0.5 mol/L NaOH, increasing the temperature of the saury to 53° C., adding Alcalase 2.4 L of Novazymes, Flavourzyme 500 MG of Novozymes, and phenylalanine as much as 0.5%, 1.5% and 0.3% of the mass of the saury precipitate, respectively, insulatingly hydrolyzing at 53° C. for 9 h, adding glucose accounting for 2.5% of the mass of the saury precipitate, heating at 100° C. for 2.0 h, then centrifuging at 5000 r/min for 15-20 min, and taking the supernatant, thus obtaining the saury Maillard peptide solution.

(3) vacuum-concentrating the saury Maillard peptide solution to the 30% solid or more, and spray drying, thus obtaining the saury Maillard peptide product C.

The therapeutical effects of the saury Maillard peptide product C on the hyperuricemia in rats induced by oteracil potassium were shown in Tables 1, 2 and 3.

Contrast Example 1

A saury peptide, which was prepared as follows:

(1) Removing the head and internal organs of the saury, cleaning, mincing over a meat grinder, adding water 5 times the mass of the minced saury meat, heating and stirring at 50° C. for 1 h, then adjusting the pH value of the system to 4.2 with HCl (0.5 mol/L), continuing to stir and heat for 1.5 h, separating by centrifugation (5000 r/min, 15-20 min), discarding the supernatant and the upper fat, and collecting a precipitate;

(2) adding water 1.5 times the mass of the saury precipitate to the saury precipitate, adjusting the pH value of the system to 7.0 with 0.5 mol/L NaOH solution, raising the temperature of the saury to 50° C., adding Alcalase 2.4 L of Novazymes and Flavourzyme 500 MG of Novozymes as much as 0.8% and 1.2% of the mass of the saury precipitate, respectively, insulatingly hydrolyzing at 55° C. for 9 h, heating at 95° C. for 15 min to inactivate enzyme, then taking the supernatant after centrifuging at 5000 r/min for 15-20 min, thus obtaining the saury peptide solution.

(3) vacuum-concentrating the saury peptide solution to the 30% solid or more, and spray drying, thus obtaining the contrast product 1.

The therapeutical effects of the contrast product 1 on the hyperuricemia in rats induced by oteracil potassium were shown in Tables 1, 2 and 3.

The uric acid peak chromatogram of the contrast product 1 was shown in FIG. 1.

Contrast Example 2

A saury peptide, which was prepared as follows:

(1) Removing the head and internal organs of the saury, cleaning, mincing over a meat grinder, adding water 5 times the mass of the minced saury meat, heating and stirring at 50° C. for 1 h, then adjusting the pH value of the system to 4.2 with HCl (0.5 mol/L), continuing to stir and heat for 1.5 h, separating by centrifugation (5000 r/min, 15-20 min), discarding the supernatant and the upper fat, and collecting a precipitate;

(2) adding water 1.5 times the mass of the saury precipitate to the saury precipitate, adjusting the pH value of the system to 7.0 with 0.5 mol/L NaOH, raising the temperature of the saury to 50° C., adding Alcalase 2.4 L of Novazymes, Flavourzyme 500 MG of Novozymes, and tryptophane as much as 0.8%, 1.2% and 0.15% of the mass of the saury precipitate, respectively, insulatingly hydrolyzing at 55° C. for 9 h, heating at 95° C. for 15 min to inactivate enzyme, then taking the supernatant after centrifuging at 5000 r/min for 15-20 min, thus obtaining the saury peptide solution;

(3) vacuum-concentrating the saury peptide solution to the 30% solid or more, and spray drying, thus obtaining the contrast product 2.

The therapeutical effects of the contrast product 2 on the hyperuricemia in rats induced by oteracil potassium were shown in Tables 1, 2 and 3.

The uric acid peak chromatogram of the contrast product 2 was shown in FIG. 1.

Contrast Example 3

A saury peptide, which was prepared as follows:

(1) Removing the head and internal organs of the saury, cleaning, mincing over a meat grinder, adding water 5 times the mass of the minced saury meat, heating and stirring at 50° C. for 1 h, then adjusting the pH value of the system to 4.2 with HCl (0.5 mol/L), continuing to stir and heat for 1.5 h, separating by centrifugation (5000 r/min, 15-20 min), discarding the supernatant and the upper fat, and collecting a precipitate;

(2) adding water 1.5 times the mass of the saury precipitate to the saury precipitate, adjusting the pH value of the system to 7.0 with 0.5 mol/L NaOH, raising the temperature of the saury to 50° C., adding Alcalase 2.4 L of Novazymes and 500 MG of Flavourzyme Novozymes as much as 0.8% and 1.2% of the mass of the saury precipitate, respectively, insulatingly hydrolyzing at 55° C. for 9 h, adding glucose as much as 0.5% of the mass of the saury precipitate, heating at 121° C. for 1.0 h, then taking the supernatant after centrifuging at 5000 r/min for 15-20 min, thus obtaining the saury Maillard peptide solution;

(3) vacuum-concentrating the saury Maillard peptide solution to the 30% solid or more, and spray drying, thus obtaining the contrast product 3.

The therapeutical effects of the contrast product 3 on the hyperuricemia in rats induced by oteracil potassium were shown in Tables 1, 2 and 3.

The uric acid peak chromatogram of the contrast product 3 was shown in FIG. 1.

TABLE 1

Effects of tuna extracts acting for different duration on serum uric acid content in rats with hyperuricemia induced by oteracil potassium

| Group | Before administration | | Treatment for 10 days | | Treatment for 20 days | | Treatment for 30 days | |
| --- | --- | --- | --- | --- | --- | --- | --- | --- |
| | n | Uric acid value (μmol/L) | n | Uric acid value (μmol/L) | n | Uric acid value (μmol/L) | n | Uric acid value (μmol/L) |
| Normal group | 12 | 81.3 ± 13.2 | 12 | 78.2 ± 10.7 | 10 | 82.7 ± 7.9 | 8 | 76.9 ± 9.8 |
| Model group | 15 | 222.2 ± 21.4 | 15 | 220.3 ± 31.2$^a$ | 15 | 216.2 ± 17.0$^a$ | 14 | 218.0 ± 34.5$^a$ |
| Allopurinol group | 14 | 230.4 ± 19.1 | 14 | 89.5 ± 22.4$^b$ | 14 | 94.5 ± 13.9$^b$ | 14 | 92.8 ± 20.9$^b$ |
| Saury Maillard peptide product A | 14 | 220.6 ± 20.2 | 14 | 185.8 ± 35.3$^c$ | 14 | 171.5 ± 23.8$^b$ | 14 | 169.2 ± 20.6$^b$ |

TABLE 1-continued

Effects of tuna extracts acting for different duration on serum uric acid content in rats with hyperuricemia induced by oteracil potassium

| Group | Before administration | | Treatment for 10 days | | Treatment for 20 days | | Treatment for 30 days | |
|---|---|---|---|---|---|---|---|---|
| | n | Uric acid value (μmol/L) | n | Uric acid value (μmol/L) | n | Uric acid value (μmol/L) | n | Uric acid value (μmol/L) |
| Saury Maillard peptide product B | 14 | 227.5 ± 19.4 | 14 | 186.7 ± 35.4$^c$ | 14 | 168.2 ± 14.3$^b$ | 11 | 163.5 ± 33.8$^b$ |
| Saury Maillard peptide product C | 14 | 220.2 ± 18.0 | 14 | 183.1 ± 27.1$^c$ | 14 | 173.7 ± 23.8$^b$ | 12 | 169.3 ± 23.8$^b$ |
| Contrast product 1 | 14 | 220.4 ± 27.2 | 14 | 208.6 ± 24.5$^c$ | 13 | 190.0 ± 21.3$^c$ | 12 | 190.8 ± 19.9$^c$ |
| Contrast product 2 | 14 | 216.0 ± 24.5 | 14 | 200.2 ± 30.1$^c$ | 12 | 182.2 ± 23.8$^c$ | 10 | 185.2 ± 16.6$^c$ |
| Contrast product 3 | 14 | 229.1 ± 20.8 | 14 | 188.1 ± 31.0$^c$ | 12 | 174.7 ± 18.3$^b$ | 10 | 172.2 ± 19.3$^b$ |

Note:
Compared with the normal group: $^a$p < 0.01, $^c$p > 0.05;
compared with the model group: $^b$p < 0.01, $^e$p < 0.05, $^f$p > 0.05.

TABLE 2

Effects of tuna extracts acting for 30 days on serum creatinine and urea nitrogen content in rats with hyperuricemia induced by oteracil potassium

| Group | Number of animals | Creatinine (μmol/L) | Urea nitrogen (mmol/L) |
|---|---|---|---|
| Normal group | 8 | 37.5 ± 6.6 | 112.6 ± 30.2 |
| Model group | 14 | 58.3 ± 11.4$^a$ | 192.7 ± 48.2$^a$ |
| Allopurinol group | 14 | 41.8 ± 13.2$^b$ | 159.2 ± 24.6$^b$ |
| Saury Maillard peptide product A | 14 | 50.4 ± 8.6$^b$ | 149.0 ± 30.6$^b$ |
| Saury Maillard peptide product B | 11 | 47.8 ± 10.4$^b$ | 141.2 ± 38.7$^b$ |
| Saury Maillard peptide product C | 11 | 49.9 ± 20.5$^b$ | 141.5 ± 28.7$^b$ |
| Contrast product 1 | 12 | 54.5 ± 10.2$^c$ | 167.2 ± 26.5$^c$ |
| Contrast product 2 | 10 | 55.3 ± 8.1$^c$ | 159.1 ± 22.6$^b$ |
| Contrast product 3 | 10 | 51.4 ± 12.8$^b$ | 156.4 ± 32.2$^b$ |

Note:
Compared with the normal control group:
$^a$p < 0.01; compared with the model group:
$^b$p < 0.01,
$^c$p < 0.05,
$^f$p > 0.05.

TABLE 3

Effects of example and contrast products acting for 30 days on serum ADA and XOD contents in rats with hyperuricemia induced by oteracil potassium

| Group | Number of animals | ADA (U/ml) | XOD (U/L) |
|---|---|---|---|
| Normal group | 8 | 7.31 ± 5.25 | 15.48 ± 2.65 |
| Model group | 14 | 17.71 ± 7.03$^a$ | 35.02 ± 5.18$^a$ |
| Allopurinol group | 14 | 12.28 ± 7.88$^b$ | 8.61 ± 2.46$^b$ |
| Saury Maillard peptide product A | 14 | 12.08 ± 7.79$^b$ | 17.28 ± 6.36$^b$ |
| Saury Maillard peptide product B | 11 | 10.71 ± 6.55$^b$ | 15.89 ± 5.93$^b$ |
| Saury Maillard peptide product C | 11 | 11.66 ± 6.31$^b$ | 19.63 ± 4.24$^b$ |
| Contrast product 1 | 12 | 15.38 ± 6.07$^c$ | 25.88 ± 5.82$^c$ |
| Contrast product 2 | 10 | 15.68 ± 5.33$^c$ | 26.63 ± 5.62$^c$ |
| Contrast product 3 | 10 | 13.51 ± 7.64$^b$ | 23.53 ± 5.22$^c$ |

Note:
Compared with the normal control group:
$^a$p < 0.01; compared with the model group:
$^b$p < 0.01,
$^c$p < 0.05,
$^f$p > 0.05.

During the metabolism of purine in the human body, hypoxanthine and xanthine is generated from ATP or other substances through a series of metabolic reactions, both of which will be oxidized into uric acid by xanthine oxidase (XOD) in the human body, thus the generation of uric acid would be inhibited by inhibiting the activity of xanthine oxidase, results in reduce of uric acid level in the body.

The present invention adopted the method of in vitro high-performance liquid chromatography to determine the inhibition of xanthine oxidase, which was as follows: First, mixing the sample with xanthine oxidase to make them interact; The amount of uric acid produced in the xanthine hydrolysis system would be reduced if the sample could interact with xanthine oxidase and inhibit the activity of the enzyme, Thus the inhibition rate of xanthine oxidase could be calculated by detecting the amount of uric acid produced.

As FIG. 1 shows, the products obtained from examples and contrast examples could inhibit the activity of xanthine oxidase compared with the blank group (PBS), but different products exhibited distinctly different inhibition rates. The xanthine oxidase inhibition rate of the contrast product 1 is 10.40%, which indicated that the protein peptide product with certain antihyperuricemic activity could be obtained by hydrolyzing saury protein through enzymolysis; the xanthine oxidase inhibition rate of the contrast product 2 was increased to 12.34%, which was increased about 18.7%. The main difference between the contrast products 1 and 2 is the addition of monomer amino acids before enzymolysis of the product 2; with progress of the enzymolysis, monomer amino acids can display substrate inhibition on the enzymolytic system, during the enzymolytic process alter the amino acid composition of the final hydrolysate, and thereby improve the antihyperuricemic activity. The xanthine oxidase inhibition rate of the contrast product 3 was significantly improved compared to the products 1 and 2; the contrast product 3 was added reducing sugar to have the Maillard reaction compare to the contrast product 1, indicated that some substances with high antihyperuricemic activity was generated from saury hydrolysates during Maillard reaction. Above knowable, the saury hydrolysate has a certain antihyperuricemic effect, and both the addition of monomer amino acids for synergistic hydrolysis and the Maillard reaction of the hydrolysate can improve its antihyperuricemic activity. Therefore, the xanthine oxidase inhibition rate of the saury Maillard peptide B (Example 2) prepared by the combination of the three methods was as high as 25.59%.

As Table 1 shows, the serum uric acid content was significantly increased ($p<0.01$) in the model rats treated with oteracil potassium for nearly 40 days, but was significantly decreased ($p<0.01$) after the rats were treated with allopurinol, which was mainly because allopurinol is a medicine that reduces uric acid production and serum uric acid concentration by inhibiting the xanthine oxidase activity. While the other administration groups (example products and contrast products) all had the significant effect of reducing serum uric acid in rats. Generally, the example products exhibited higher antihyperuricemic activity than the contrast products.

Table 2 shows that the serum creatinine and urea nitrogen content of rats after administration. The results indicated that each example product could significantly reduce the serum creatinine and urea nitrogen content in the rats ($p<0.01$). Serum creatinine is the product of human muscle metabolism and urea nitrogen is the main end product of human protein metabolism. Under normal circumstances, both of them are excreted through kidneys by glomerular filtration, and their level in plasma indicated renal function. The above results indicated that the saury Maillard peptide prepared by the process of the present invention had an effect in significantly decreasing the serum creatinine level, and had a certain protective effect in the renal function of the hyperuricemia model rats.

Xanthine oxidase (XOD) and adenosine deaminase (ADA) are key enzymes in uric acid metabolism. Wherein XOD widely exists in a variety of animals and human body. Liver has the highest content of XOD, followed by the small intestine, while the content of XOD in the rest of tissues is less than 3% of the content in the liver and small intestine. XOD can directly regulate uric acid levels in the body by subsequently oxidizing Xanthine and hypoxanthine into uric acid. The adenosine is catalyzed by ADA into hypoxanthine nucleotide and is finally oxidized by XOD into uric acid. The increase in activity of XOD and ADA contributes to promotion of the nucleic acid catabolism and the production of uric acid. As Table 3 shows, when the model rats were treated with oteracil potassium for nearly 40 days, the activity of serum xanthine oxidase (XOD) and adenosine deaminase (ADA) in the model rats was significantly increased ($p<0.01$). The example products (the saury Maillard peptides A, B and C) showed a strong effect on reducing serum ADA and XOD activity in rats; the contrast products, although also having a certain effect on reducing these two enzymes, had an overall effect inferior to that of the example products.

In conclusion, the antihyperuricemic peptide prepared according to the present invention has the effect in reducing the levels of urea nitrogen and creatinine which are high in the serum of rats suffered from hyperuricemia-induced kidney injury, suggesting that it has certain protective effect on renal function. Besides, it can reduce the XOD and ADA enzyme activity in serum, suggesting that it reduces the activity of key enzymes so as to reduce the catabolism of nucleic acids and to decrease the uric acid production. Therefore, the antihyperuricemic peptide prepared by the method of the present invention has a good application prospect.

The above examples are preferred embodiments of the present invention; however, the embodiments of the present invention are not limited by the above examples, and any other alteration, modification, substitution, combination and simplification made without departing from the spiritual essence and principle of the present invention are equivalent replacements and fall within the scope of protection of the present invention.

What is claimed is:

1. A method of preparing a saury Maillard peptide with antihyperuricemic activity, comprising:
   (1) pretreatment of saury: removing head and internal organs of the saury, cleaning, mincing in a meat grinder, adding water 3 to 5 times the mass of the minced saury meat, heating and stirring at 40° C. to 50° C. for 1 to 2 h, adjusting a pH value of the mixture to 4.2, continuing to stir and heat for 1 to 1.5 h, separating by centrifugation, discarding the supernatant and the upper fat, and collecting a precipitate; and
   (2) enzymolysis-Maillard continuous reaction: adding water 1 to 1.5 times the mass of the saury precipitate to the saury precipitate, then adding protease and monomer amino acids, adjusting the pH value of the mixture to 7.0, hydrolyzing at 50° C. to 55° C. for 6 to 9 h, adding reducing sugar, heating at 100° C. to 121° C. for 1.0 to 2.0 h, and centrifuging, to obtain a saury Maillard peptide solution; and vacuum-concentrating and spray drying the peptide solution, thus obtaining saury Maillard peptide dry powder;
   calculated based on the mass of the saury precipitate, the amount of the added protease accounts for 1.5% to 3.0%, the amount of the added monomer amino acids accounts for 0.1% to 0.3%, and the amount of the added reducing sugar accounts for 0.5% to 2.5%;
   the monomer amino acids described in step (2) are tyrosine, phenylalanine or tryptophan; and
   the reducing sugar described in step (2) is glucose, xylose or ribose.

2. The method of preparing the saury Maillard peptide having antihyperuricemic activity according to claim 1, wherein the protease described in step (2) is an alkaline protease and a flavourzyme.

\* \* \* \* \*